March 2, 1943. P. DE VOR Plant Pat. 569
ROSE PLANT
Filed Sept. 12, 1942
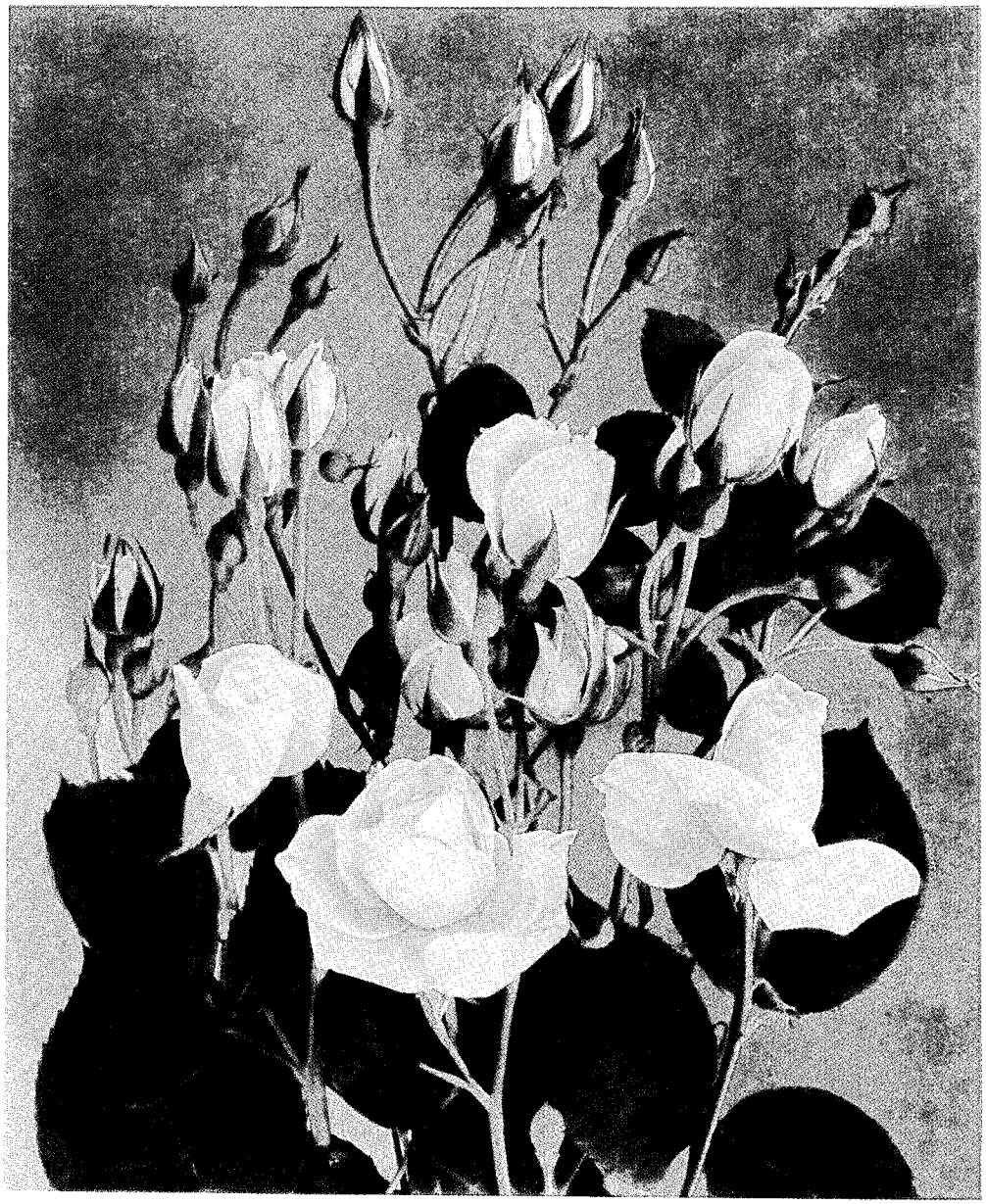
Inventor
Paul De Vor
By Robbins & Robb
Attorneys Patented Mar. 2, 1943

Plant Pat. 569

UNITED STATES PATENT OFFICE

569

ROSE PLANT

Paul De Vor, Pleasanton, Calif., assignor to Jackson & Perkins Company, Newark, N. Y., a corporation of New York Application September 12, 1942, Serial No. 458,108

1 Claim. (Cl. 47—61)

The present discovery relates to a new and distinct variety of polyantha rose plant, originating as a sport which I found growing upon a plant of the variety known as "Pinocchio," described in detail in Plant Patent No. 484, dated August 12, 1941.

While in certain respects this new variety is similar to its parent, its predominating distinction therefrom is found in the unusual coloring of its flowers—Straw Yellow in the unfurling bud, and Barium Yellow in the opening flower, fading to almost clear White when fully open. It is noted that the flowers of the parent variety are a Geranium Pink suffused with Apricot Yellow.

The number, appearance and form of the petals, as well as the coloring of the foliage and form and color of the thorns, are other points of important distinction, as will be more specifically pointed out in the detail description of this new variety herein given, the foregoing characteristics having been found to come true to form in asexual reproductions of the new rose.

In the following detail description, color terminology accords with Ridgway's Color Standard:

Parentage: Sport.

*Parent variety.*—"Pinocchio."

Classification:

*Botanic.*—Large flowered polyantha.

*Commercial.*—Floribunda.

*Flower*

(Observations made in the fields of Jackson & Perkins Company, Newark, New York, in the morning of June 8, 1942.)

Blooming habit: Recurrent—continuous.

Bud:

*Size.*—Small.

*Form.*—Short; ovoid. Is not affected by wet or hot weather.

*Color.*—When sepals first divide—Martius Yellow, Plate 4. When petals begin to unfurl—Straw Yellow, Plate 16. When half blown, inside of petals—Naphthalene Yellow, Plate 16, lower half of petal Barium Yellow, Plate 16; reverse of petals—Barium Yellow, Plate 16, lower half of petal Citron Yellow, Plate 16.

*Sepals.*—Serrated, branched; curl back when petals unfurl; Inside, Pale Glass Green, Plate 31, outside, Courge Green, Plate 17.

*Calyx.*—Shape—funnel, *Size*—small. *Aspect*—smooth. *Color*—Cosse Green, Plate 5.

*Peduncle.*—*Length*—medium. *Aspect*—smooth. *Color*—Cosse Green, Plate 5. *Strength*—stiff; slender.

*Opening.*—Bud opens well. Is not affected by adverse conditions.

Bloom:

*Size.*—Medium. Average size when fully expanded—2½ inches.

*Borne.*—In clusters, irregular.

*Stems.*—Medium length; strong.

*Form.*—When first open—cupped. *Permanence*—outer petals curl back.

*Petalage.*—Double (full but open center). Number of petals under normal conditions—25 to 30.

*Color.*—Center of flower—Straw Yellow, Plate 16. Outer petals—Naphthalene Yellow, Plate 16. Base of petals (aiglet)—Pale Lemon Yellow, Plate 4. Inside of petals—Massicot Yellow, Plate 16, lower half of petal Barium Yellow, Plate 16. Reverse of petals—Naphthalene Yellow, Plate 16, lower half of petal Barium Yellow, Plate 16. General tonality from a distance—between Amber Yellow, Plate 16, and Straw Yellow, Plate 16.

*Discoloration.*—General tonality at end of first day—Barium Yellow, Plate 16. Second day—Naphthalene Yellow, Plate 16. Third day—White, Plate 53, tinged with Marguerite Yellow, Plate 30.

Petals:

*Texture.*—Thick. Is not affected by wet or hot weather.

*Appearance.*—Inside—satiny. Outside—shiny.

*Form.*—Oval.

*Arrangement.*—Imbricated (regularly arranged shingle-like). Petaloids in center—few; small.

*Persistence.*—Drop off cleanly.

*Fragrance.*—Very slight; wild rose.

*Lasting quality.*—On the plant and as cut flower—long.

Genital organs: Stamens, anthers—medium size; few.

*Color.*—Light Cadmium, Plate 4.

*Arrangement.*—Regular around styles.

*Stamens, filaments (threads).* — Short. *Color*—Apricot Yellow, Plate 4.

*Pollen.*—Apricot Yellow, Plate 4.

*Styles.*—Bunched; uneven length; short; thin.
*Stigmas.*—Picric Yellow, Plate 4.
*Ovaries.*—All enclosed in calyx.

*Plant*

Form: Bush.
Growth: Vigorous; compact.
Foliage: 5 leaflets.
*Size.*—Medium.
*Quantity.*—Abundant.
*Color.*—New foliage: upper side—Cress Green, Plate 31; under side—Light Cress Green, Plate 31. Old Foliage: upper side—Lettuce Green, Plate 5; under side—Kildare Green, Plate 31.
*Shape.*—Oval pointed.
*Texture.*—Upper side—leathery. Under side—smooth. Ribs and veins—ordinary.
*Edge.*—Serrated (saw toothed).
*Serration.*—Single; small.
*Rachis.*—*Color*—Cress Green, Plate 31 Under side—prickles.
*Stipules.*—Medium length; smooth.
*Disease resistance.*—Resistant insofar as this is evidenced by absence of any disease throughout development and establishment of this variety.

Wood:
*New Wood.*—*Color*—Light Cress Green, Plate 31. Bark—smooth.
*Old Wood.*—*Color*—Cress Green, Plate 31. Bark—smooth.

Thorns (thorns are divided into thorns, prickles and short needles):
*Thorns.*—*Quantity,* on main stalks from base—ordinary; on laterals from stalk—few. *Form*—narrow base; hooked downward. *Color when young*—Chrysolite Green, Plate 31. *Position*—irregular.
*Prickles.*—On main stalks and on laterals—none.
*Short needles.*—On main stalks and on laterals—none.

I claim:

A new and distinct variety of polyantha rose plant, characterized predominantly as to novelty by the unusual coloring of its flowers, specifically Straw Yellow in the unfurling bud and Barium Yellow in the opening flower, fading to almost clear White when fully open as compared with the varying Pink of its parent variety, substantially as shown and described.

PAUL DE VOR.